United States Patent [19]

Rasp et al.

[11] 4,058,556

[45] Nov. 15, 1977

[54] PROCESS FOR THE PREPARATION OF ACETOXYBUTANAL

[75] Inventors: Christian Rasp, Cologne; Gerhard Scharfe; Johann Grolig, both of Leverkusen, all of Germany

[73] Assignee: Bayer Aktiengesellschaft, Leverkusen, Germany

[21] Appl. No.: 588,079

[22] Filed: June 18, 1975

[30] Foreign Application Priority Data

June 22, 1974 Germany .............................. 2430082

[51] Int. Cl.$^2$ ............................................ C07C 67/28
[52] U.S. Cl. ................................ 560/231; 260/635 A
[58] Field of Search ......................... 260/491, 632 HF

[56] References Cited

U.S. PATENT DOCUMENTS

| | | | |
|---|---|---|---|
| 3,231,621 | 1/1966 | Slaugh | 260/604 HF |
| 3,287,400 | 11/1966 | Hagemeyer et al. | 260/491 |
| 3,904,547 | 9/1975 | Aycock et al. | 260/638 HF |

*Primary Examiner*—Vivian Garner
*Attorney, Agent, or Firm*—Burgess, Dinklage & Sprung

[57] ABSTRACT

Process for the preparation of acetoxybutanal by reaction of allyl acetate with carbon monoxide and hydrogen under pressure and at elevated temperature, in the presence of a metal carbonyl compound. The reaction is carried out at 130° to 180° C and at concentrations of allyl acetate of less than 20% by weight, relative to the liquid phase. High yields are obtained.

8 Claims, No Drawings

PROCESS FOR THE PREPARATION OF ACETOXYBUTANAL

RELATED APPLICATIONS

Application Ser. No. 588,078, filed June 18, 1975; application Ser. No. 588,080, filed June 18, 1975, abandoned; and application Ser. No. 588,077, filed June 18, 1975, now U.S. Pat. No. 4,016,201, all assigned to the assignee hereof and directed to related subject matter.

The present invention relates to a process for the preparation of acetoxybutanal by catalytic reaction of allyl acetate with carbon monoxide and hydrogen.

Acetoxybutanal is a valuable starting material for the preparation of butanediol. Butanediols are industrially used solvents and intermediates in the preparation of polyurethanes, epoxide resins, polyesters, polyamides and plasticisers. 1,4-butanediol is particularly suitable for the preparation of polyurethanes and thermoplasts (Kirk-Othmer, Encyclopedia of Chemical Technology, 2nd Ed., Vol. 10, 672 (1966)). 1,2-Butanediol can be processed to alkyd resins (U.S. Pat. No. 2,965,587); 2-methyl-1,3-propanediol is a valuable starting material for the production of polyesters from which dyeable fibres can be manufactured (French Specification No. 1,303,888). Butanediol can be obtained from acetoxybutanal by hydrogenation and subsequent hydrolysis.

It is known, from a publication by Adkins and Krsek, J. Amer. Chem. Soc., 70, (1948), page 383, to heat a mixture of allyl acetate, solvent and dicobalt octacarbonyl with carbon monoxide and hydrogen under pressure to temperatures of at most 125° C. Acetoxybutanal can be obtained in a yield of 69% in this reaction.

For industrial application of the process of preparation of acetoxybutanal by reaction of allyl acetate with carbon monoxide and hydrogen it is important to achieve improved yields of acetoxybutanal.

THE INVENTION

It has now been found that, in accordance with this invention, allyl acetate can be reacted with carbon monoxide and hydrogen under pressure, usually from 20 to 1000 bars, e.g. 70–1000 bars and at an elevated temperature, in the presence of a metal carbonyl compound, to give high yields of acetoxybutanol, if the reaction is carried out at a temperature of from 130° to 180° C and at an allyl acetate concentration of less than 20% by weight, relative to the liquid phase, substantially throughout the reaction.

Preferably, the temperature is from 140° to 160° C and the pressure is from 50 to 500 bars. The use of pressures of 100 to 300 bars is very particularly preferred. The ratio of carbon monoxide/hydrogen is preferably within the range 2:1 to 1:2. Suitable residence times are from 0.2 to 60 minutes. It is advantageous to ensure good mixing of the gas phase and the liquid phase.

The reaction can be carried out in the presence of a solvent, for example xylene. Other suitable solvents are toluene, benzene, cyclohexane, methylcyclohexane, dimethylcyclohexane. Through the presence of a solvent, homogeneous mixing of the reaction components and the required dilution of the allyl acetate are achieved.

The reaction is carried out in the presence of carbonyl-forming metals of the transition elements, or of their compounds. Transition elements which may be mentioned are iron, cobalt, nickel, chromium, molybdenum, tungsten, rhenium, manganese, ruthenium, osmium, rhodium, iridium, vanadium, titanium, copper, palladium and platinum.

The catalysts can be prepared in situ by introducing the transition elements, in the form of the metal or in the form of their compounds, into the reaction chamber in which they can react with the carbon monoxide/hydrogen mixture to give metal carbonyl compounds. Suitable compounds of the transition elements are a very great variety of inorganic and organic salts of the metals, such as oxides, hydroxides, carbonates, carboxylates, acetylacetonates, naphthenates, oleates and stearates, as well as carbonyl compounds, carbonylhydrides or complex compounds. The following may be mentioned as individual compounds: cobalt carbonate, cobalt oxide, cobalt formate, cobalt acetate, cobalt oleate, cobalt acetylacetonate, cobalt naphthenate, iron acetylacetonate, manganese acetylacetonate, rhodium trichloride and the complexes of vanadium with tributyl phosphite, rhodium with triethyl phosphite, chromium with trimethylarsine, cobalt with triphenylphosphine and palladium with o-methyldiphenylarsinite, as well as carbonyls and carbonyl-hydrides, such as $Ni(CO)_4$, $Fe(CO)_5$, $Co_2(CO)_8$, $Mo(CO)_6$, $Cr(CO)_6$, $W(CO)_6$, $Re_2(CO)_{10}$, $Mn_2(CO)_{10}$, $Os(CO)_5$, $[Rh(CO)_3]_4$, $HCo(CO)_4$, $H_2Fe(CO)_4$, $HMn(CO)_5$, $HRe(CO)_5$ and $HRh(CO)_4$.

The concentration of the catalysts in the reaction mixture can be varied within wide limits. Thus, it may be from 0.002 to 10% by weight, for example 0.1 to 1% by weight, based on the liquid phase in the reactor.

The concentration of allyl acetate, based on the liquid phase, is adjusted to less than 20% by weight. The concentration of allyl acetate can be, for example, 0.1–10% by weight, preferably 0.5 to 2% by weight, based on the liquid phase. High yields of acetoxybutanal can be achieved by the measures according to the invention. The yield can be 90 to 99%, for example 93 to 98%. It is possible to achieve a conversion of more than 99%, relative to allyl acetate. After completion of the reaction the acetoxybutanal can be separated from the catalyst, for example by distillation. The catalyst can, if necessary after a pretreatment, be recycled to the reaction.

The reaction of allyl acetate with $CO/H_2$ to give acetoxybutyraldehyde can be carried out discontinuously or continuously. To achieve high space-time yields and selectivities it is advantageous to react the catalyst in a separate stage by reacting a metal compound, for example a cobalt compound such as cobalt acetylacetonate, in a solubilising agent, for example cyclohexane or xylene, with carbon monoxide and hydrogen at elevated pressure and elevated temperature, for example 200 bars and 150°–170° C, to give an active catalyst solution. If the process is carried out continuously, the two product streams, namely catalyst solution and allyl acetate, are then pumped continuously into the reaction vessel and the reaction of allyl acetate with carbon monoxide and hydrogen is carried out therein in the presence of the catalyst solution. In this way, improved values of the space-time yield and selectivity are obtained, as compared to those obtained if the preparation of the catalyst is carried out in the presence of allyl acetate.

If the process is carried out discontinuously, the procedure followed can be to introduce a metal compound which forms metal carbonyl compounds with monoxide and hydrogen, in a suitable solvent, for example xylene, into the reaction vessel and bring it, together with hydrogen and carbon monoxide, to the desired working conditions, for example 130° to 150° C, and a suitable pressure of, for example, 200–300 bars. Allyl acetate is then introduced into the reactor at a rate such that the concentration of allyl acetate, relative to the liquid phase, is less than 20% by weight. Care must be taken that the heat of reaction should be removed and that the temperature should remain in the range from 130° to 180° C.

If the process is carried out continuously, the active catalyst solution and allyl acetate are pumped into the reactor, at temperatures of from 130° to 180° C, at a rate such that the concentration of allyl acetate, based on the liquid phase, is less than 20% by weight. During the reaction, intimate mixing of the liquid phase and gas phase, and good removal of the heat of reaction, must be ensured. In a preferred embodiment of the process, the addition of allyl acetate is so controlled that the concentration of allyl acetate, relative to the liquid phase, is about 0.1 to 10% by weight, preferably 0.5 to 2% by weight, relative to the liquid phase.

Furthermore, in carrying out the process continuously, a stream of carbon monoxide/hydrogen mixture, allyl acetate and active catalyst solution is introduced into the reactor, and a liquid reaction mixture consisting essentially of acetoxybutanal and containing catalyst is withdrawn. The active catalyst can also be added by introducing a small amount of gaseous catalyst, for example cobalt carbonyl-hydride, into the carbon monoxide/hydrogen gas stream.

After completion of the reaction, the catalyst is separated off and the acetoxybutanal is discharged as the end product. It can, if desired, be converted to butanediol by subsequent hydrogenation and hydrolysis.

EXAMPLE 1

6 g of cobalt-II acetylacetonate in 200 ml of o-xylene are treated for 30 minutes in an autoclave at 170° C, whilst stirring, with a $CO/H_2$ mixture in the molar ratio of 1:1, and a pressure of 200 bars. The temperature is then lowered to 140° C. 200 g of allyl acetate are pumped in over the course of 20 minutes. The velocity of the allyl acetate addition corresponds to the addition of $CO/H_2$ which again corresponds to the pressure being necessary for maintaining the pressure conditions of the reaction, both the addition of the allyl acetate and the addition of CO and $H_2$ as to the amounts, being based on the stoichiometric equation for the chemical reaction. The content of allyl acetate in the solution (weight % of allyl acetate) can be calculated from the molar ratio allyl acetate : $CO/H_2$ existing at any particular point during the reaction. The pressure is kept at 200 bars by addition of $CO/H_2$ mixture. The heat of reaction is removed by cooling and the temperature is kept at 140° C. Ten minutes after completing the pumping-in of the allyl acetate, the mixture is cooled to room temperature and the pressure is released. An allyl acetate conversion of 99.8% was achieved in the reaction. Acetoxybutanal was produced in a yield of 94 mol %, based on allyl acetate employed. The acetoxybutanal obtained is passed, without separation into the individual isomers, to the next use stage, for example the hydrogenation and subsequent hydrolysis to butanediol. According to analysis by gas chromatography, the acetoxybutanal obtained consists of the following three isomeric aldehydes: 4-acetoxybutanal, 2-acetoxybutanal and 3-acetoxy-2-methylpropanal; these can, if desired, be separated by distillation.

EXAMPLE 2 — comparison 6 g of cobalt-II acetylacetonate in 200 ml of o-xylene and 200 g of allyl acetate are heated from 20° C to 140° C in the course of 20 minutes in an autoclave, together with a $CO/H_2$ mixture in the molar ratio of 1:1 and a pressure of 200 bars. The pressure is kept at 200 bars by addition of $CO/H_2$ mixture. The reaction is carried out for 30 minutes at 140° C whilst stirring and cooling to remove the heat of reaction. The mixture is then cooled to room temperature and the pressure is released. An allyl acetate conversion of 44% was achieved in the reaction. Acetoxybutanal was produced in a yield of 91 mol %, calculated relative to allyl acetate converted. According to analysis by gas chromatography, the acetoxybutanal obtained consists of 4-acetoxybutanal, 2-acetoxybutanal and 3-acetoxy-2-methylpropanal.

What we claim is:

1. In a process for the preparation of acetoxybutanal by reaction of allyl acetate with carbon monoxide and hydrogen under pressure and at elevated temperature, in the presence of a cobalt carbonyl compound and a solvent, the improvement which comprises, the reaction being carried out at 130° to 180° C and at concentrations of allyl acetate of less than 20% by weight, relative to the liquid phase, substantially throughout the reaction.

2. Process according to claim 1, characterised in that the reaction is carried out at a concentration of allyl acetate of 0.1 to 10% by weight, relative to the liquid phase.

3. Process according to claim 1, characterised in that the reaction is carried out at a concentration of allyl acetate of 0.5 to 2% by weight, relative to the liquid phase.

4. Process of claim 3, wherein the pressure is 70–1000 bars.

5. Process according to claim 1, characterised in that the cobalt carbonyl compound is a gaseous compound mixed with the gaseous carbon monoxide and hydrogen.

6. Process according to claim 1, characterised in that the pressure is 20 – 1000 bars.

7. Process according to claim 1, wherein the solvent is o-xylene and the temperature is 140° C and the pressure is 200 bars.

8. Process of claim 1 wherein the cobalt carbonyl compound is one which has been prepared in a separate stage by reaction of a cobalt compound with carbon monoxide and hydrogen at 150°–170° C at an elevated pressure.

* * * * *